United States Patent [19]

Wojcik

[11] Patent Number: 4,823,805

[45] Date of Patent: Apr. 25, 1989

[54] CATHETER INCORPORATING STRAIN RELIEF

[75] Inventor: Dennis Wojcik, San Diego, Calif.

[73] Assignee: C. R. Bard, Inc., Murray Hill, N.J.

[21] Appl. No.: 4,157

[22] Filed: Jan. 16, 1987

Related U.S. Application Data

[63] Continuation of Ser. No. 761,975, Aug. 1, 1985.

[51] Int. Cl.⁴ ............................................ A61M 25/00
[52] U.S. Cl. .................................... 128/736; 604/282
[58] Field of Search ............................... 604/280–284; 128/736, 724

[56] References Cited

U.S. PATENT DOCUMENTS 4,632,125 12/1986 Webler et al. .................. 128/736 X
4,730,623 3/1988 Lee ................................... 128/736 X Primary Examiner—Dalton L. Truluck
Attorney, Agent, or Firm—Freilich, Hornbaker, Rosen & Fernandez

[57] ABSTRACT

A catheter including an internal sensing wire extending along most of the length of an easily stretched catheter body having a multifilament, strain relief line affixed in the catheter body parallel to said wire. The strain relief line has sufficient tensile strength to prevent the sensing wire from breaking under moderate tensile loading.

8 Claims, 1 Drawing Sheet

CATHETER INCORPORATING STRAIN RELIEF

This is a continuation of co-pending application Ser. No. 06/761,975 filed on 8/01/85.

BACKGROUND OF THE INVENTION

Catheters used for medical applications typically have elongated bodies formed of soft flexible materials, such as latex blends or silicone. Such catheters typically include a passage for draining fluid from a first end inserted into a patient's body cavity to a second end coupled to some utility device, e.g. a collection container.

Frequently such catheters include a temperature sensor mounted in the catheter body proximate to the first end. In such catheters, sensor wires internal to the catheter body extend from the temperature sensor to proximate the second end. Unfortunately, tensile loads typically produced by restless patients exceed the tensile strength of, and thus break, the sensor wires, thereby rendering the sensor inoperative. Moreover, the broken wires frequently deform, and sometimes penetrate, the outer surface of the catheter body thus creating the possibility of patient tissue damage.

SUMMARY OF THE INVENTION

The present invention is directed to improvements in a catheter having wires mounted therein for protecting the wires against breakage attributable to tensile loading.

In accordance with the invention, a transducer (e.g. temperature sensor) carrying catheter is provided including a flexible strain relief line lying within the catheter body and attached thereto extending along most of the length of the catheter body.

In accordance with the preferred embodiment, the strain relief line has a smaller ratio of elongation to tensile load than the transducer wire so that, when subjected to a tensile load, the strain relief line limits elongation of the catheter body and therefore protects the wire against breaking.

The novel features of the invention are set forth with particularity in the appended claims. The invention will be best understood from the following description when read in conjunction with the accompanying drawings.

DESCRIPTION OF AN EXEMPLARY EMBODIMENT

Figure 1:
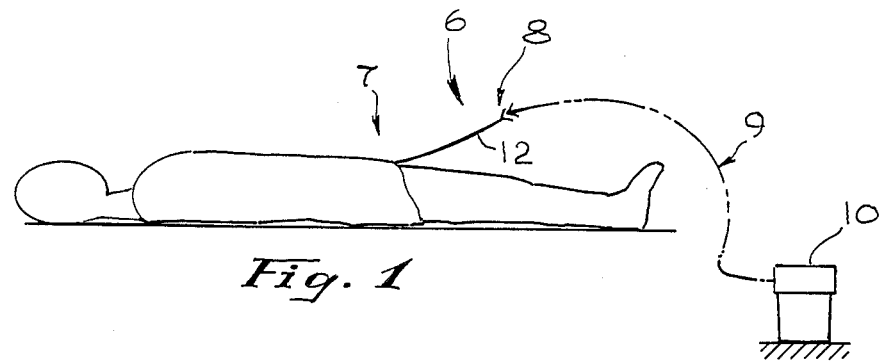
FIG. 1 is a schematic illustration depicting a typical use of a medical catheter to couple a patient to a utility device.

FIG. 1 illustrates an exemplary catheter 6 having a first end 7 intended for insertion into a patient's body cavity and a second end 8 for coupling, via tubing 9, to some utility device 10 such as a collection container. For purposes of description the exemplary catheter 6 will be assumed to be a Foley catheter used for draining urine from a patient's bladder and having a temperature sensor mounted near its first end 7 for measuring internal bladder temperature.

The catheter 6 includes an elongated body 12 formed of soft and pliable elastomeric material. A suitable formulation is composed of about 70% latex and 30% Teflon, so that the catheter has sufficient stiffness for insertion into the patient's body but is easily deflected by body tissue without causing tissue damage. A typical catheter of this type has a length on the order of 16 inches (40 cm).

Figure 2:
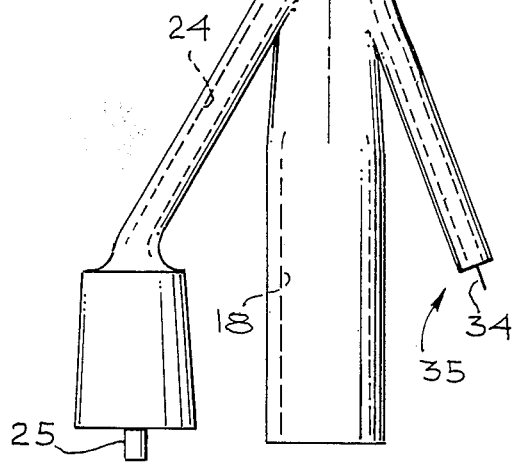
FIG. 2 is a side view of a catheter in accordance with the present invention partially broken away to show internal sectional views.

As depicted in FIG. 2, the catheter 6 includes a main passage 18 opening to an eyelet 20 at the first end 7, for receiving fluid from the patient's body cavity, e.g. bladder. A balloon 22 is mounted close to the first end 7 and communicates with a second passage 24, extending along most of the length of the catheter body via an opening 26. The second end of passage 24 opens at coupling 25 through which liquid (e.g. water) can be supplied to inflate the balloon 22 to position 22A to hold the catheter in place in the body cavity.

The catheter has a third passage 28 which accommodates a sensing assembly 30. The sensing assembly includes a transducer such as a temperature sensing thermistor 32 mounted near the first end 7 of the catheter. The sensing assembly also includes at least one insulated wire 34 which extends from the thermistor 32 through the passage 28 and emerges at 35 near the second end 8 for connection to a utility device 9 which may comprise a measuring instrument.

The soft pliable catheter body 12 bends easily to enable it to be inserted without causing tissue damage and also stretches readily when a tensile load is applied between its ends. Active or restless patients frequently subject emplaced prior art catheters to tension loads which, though within the tensile strength of the elastomeric catheter body material, exceed the tensile strength (typically, less than 10 lbs.) of the delicate sensor wires 34. Accordingly, when tension is applied to the catheter, the body 12 readily stretches and the load must then be borne by the sensor wires 34 which have a considerably lower coefficient of elasticity. When a wire 34 breaks, it of course renders the temperature sensor inoperative, but after breaking, and when tension on the catheter is lessened, the resulting contraction of the catheter causes the broken wire to bunch in an accordian like manner, creating a series of ridges in the outer surface of the catheter body. These projecting ridges can cause discomfort to the patient during removal of the catheter. Further, the broken wire end can penetrate the soft catheter body material and protrude through the outer surface of the catheter creating the potential for tissue damage.

Many unsuccessful attempts have been made to prevent breaking of the sensing wires. For example, it might be thought sufficient to use thicker sensing wires that would bear greater tensile loads. However, wires having acceptable tensile and electrical characteristics have not been found which can be accommodated in the wire channel 28 which typically has a diameter of about 0.030 inches. Other attempts have involved molding a fabric mesh or coiled wire into the catheter body 12 during the molding process. These approaches however have been characterized by significant fabrication problems.

In accordance with the present invention, a pliable strain relief line 36, such as a nylon or polyester thread, is placed into the catheter body such that it remains bonded in place without slipping. Placement of the strain relief line has been successfully accomplished by molding the strain relief line into the catheter body, and also by anchoring the strain relief line alongside the sensing wires by bonding the combination strain relief and sensing wire assembly at both the first and the second ends using adhesive. Both nylon and polyester threads, exhibiting smaller ratios of elongation to tensile load than the catheter body, have been successfully used as strain relief lines to carry substantial tensile loads without elongating sufficiently to break the sensing wires 34.

In accordance with the preferred embodiment, a nylon (or polyester) thread 36 is molded into place in the catheter body. Such threads bond well to the catheter material and provide adequate strain relief to prevent wire breakage at loads which might be experienced in practice (typically under 10 pounds). Such polyester or nylon threads having a diameter of about 0.015 inch have successfully been used to provide strain relief. Each nylon or polyester thread is preferably comprised of multiple filaments (FIG. 4) to yield greater bending flexibility for a given tensile strength. Additionally, the multiple filaments provide a greater surface area (as compared with a monofilament) which therefore assures better adhesion of the thread to the surrounding catheter material. A typical urological temperature catheter has an outside body diameter of about 0.23 inch. The strain relief line has an outside diameter less than about one-tenth the body diameter, so that the line does not introduce excessive resistance to bending.

The strain relief line 36 is preferably molded into the catheter body. In latex blend embodiments, this can be accomplished by first successively dipping a mandrel into a latex blend material in a fluid state. After several dippings, the nylon or polyester thread is placed against the partially dried layer on the mandrel, and successive dipping of the mandrel continues.

Figure 3:
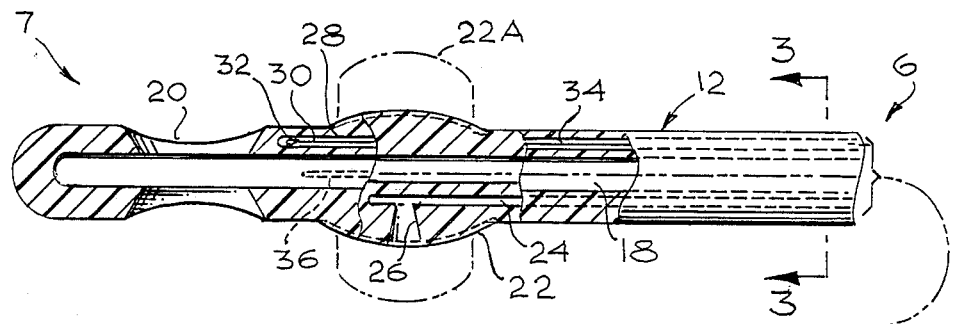
FIG. 3 is a sectional view taken on the line 3—3 of FIG. 2, rotated slightly for clarity.
Figure 3:
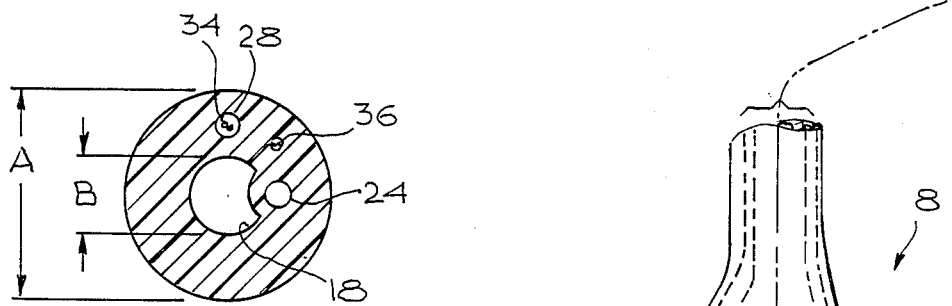
Figure 4:
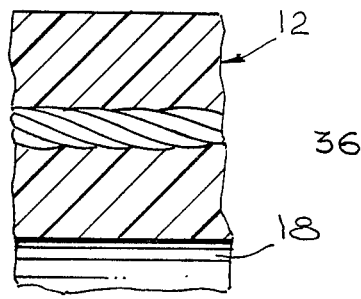
FIG. 4 is an enlarged partial sectional view of the catheter of FIG. 2 showing the strain relief line in detail.

Catheters of the type shown in FIGS. 2-4 have been successfully constructed wherein the catheter had a diameter A of about 0.23 inch and a main passage inside diameter B of about 0.10 inch. The second and third passages 24, 28 each had diameters of about 0.030 inch. The strain relief line 36 was formed of multi-filament nylon and had a diameter of about 0.015 inch. The sensing wire assembly included two insulated copper wires, each having a diameter of about 0.004 inch surrounded by insulation having a thickness of about 0.002 inch. It was found that this catheter could withstand a tension load of about 15 lbs., without the sensing wire 34 breaking. In contrast, in a conventional catheter without a strain relief line to limit elongation of the catheter body, the sensing wire is typically able to withstand only about an 8 lb. tension load.

Thus, the invention provides an improved transducer carrying catheter having internal sensing wires extending therealong which are protected against breaking by a strain relief line, such as multifilament nylon, anchored within the catheter body to limit elongation.

Although particular embodiments of the invention have been described and illustrated herein, it is recognized that modifications and variations may readily occur to those skilled in the art and consequently, it is intended that the claims be interpreted to cover such modifications and equivalents.

I claim:
1. A catheter apparatus for medical applications comprising:
   an elongated body having a first end intended to be passed through a patient's body passageway into a body cavity and a second end intended to be coupled to a utility device, said elongated body being formed of a flexible material enabling it to conform to the shape of said patients body passageway;
   a transducer mounted in said elongated body proximate to said first end; and
   a substantially straight elongated transducer wire mounted in said elongated body extending from said transducer to said second end, said transducer wire being flexible enabling it to conform to the shape of said elongated body; and
   a substantially straight elongated strain relief line mounted in and anchored to said elongated body extending substantially parallel to said transducer wire, from proximate to said first end to proximate to said second end, said strain relief line being flexible enabling it to conform to the shape of said elongated body and exhibiting a smaller ratio of elongation to tensile load than either said elongated body or said transducer wire to thereby prevent significant elongation of said elongated body whereby said transducer can be retained proximate to said first end without breaking said transducer wire.

2. The catheter apparatus of claim 1 wherein said strain relief line comprises a multifilament thread.

3. The catheter apparatus of claim 1 wherein said transducer comprises a temperature sensor.

4. The catheter apparatus of claim 1 wherein said strain relief line is molded into said elongated body.

5. The catheter apparatus of claim 1 wherein said strain relief line is bonded to said transducer wire.

6. A temperature catheter apparatus comprising:
   an elongated body of soft and pliable elastomeric material having first and second ends, said body forming a wire-receiving passage extending along most of the length of the body;
   a substantially straight sensing wire lying in said wire-receiving passage, coupled to a temperature sensor lying near the first end of said wire-receiving passage, said sensing wire being formed of flexible material for conforming to the shape of said elongated body; and
   a substantially straight elongated strain relief line mounted in and anchored to said body extending substantially parallel to said sensing wire between the first and second ends thereof, said strain relief line being flexible to conform to the shape of said elongated body and having a smaller ratio of elongation to tensile load than said body or said sensing wire to thereby prevent significant elongation of said body and resist breakage of said sensing wire without pulling said transducer away from said first end.

7. The apparatus described in claim 6 wherein:
said strain relief line comprises multiple filaments.

8. The apparatus described in claim 1 wherein:
said body is formed of a material which consists primarily of latex, and said strain relief line consists of a polymer chosen from the following materials: nylon and polyester.

* * * * *